(12) United States Patent
Custodio

(10) Patent No.: US 12,076,045 B2
(45) Date of Patent: Sep. 3, 2024

(54) SURGICAL SYSTEMS FOR PERCUTANEOUSLY INSERTING SURGICAL DEVICES

(71) Applicant: ARTHREX, INC., Naples, FL (US)

(72) Inventor: Christianne Kate Sison Custodio, Naples, FL (US)

(73) Assignee: ARTHREX, INC., Naples, FL (US)

( * ) Notice: Subject to any disclaimer, the term of this patent is extended or adjusted under 35 U.S.C. 154(b) by 508 days.

(21) Appl. No.: 17/191,011

(22) Filed: Mar. 3, 2021

(65) Prior Publication Data

US 2022/0280186 A1    Sep. 8, 2022

(51) Int. Cl.
| | |
|---|---|
| *A61B 17/16* | (2006.01) |
| *A61B 17/34* | (2006.01) |
| *A61M 25/09* | (2006.01) |
| *A61B 17/00* | (2006.01) |

(52) U.S. Cl.
CPC ...... *A61B 17/3423* (2013.01); *A61B 17/1604* (2013.01); *A61B 17/3496* (2013.01); *A61M 25/09* (2013.01); *A61B 2017/00902* (2013.01)

(58) Field of Classification Search
CPC . A61B 17/16; A61B 17/1602; A61B 17/1637; A61B 17/1695; A61B 17/3423; A61B 17/3456
See application file for complete search history.

(56) References Cited

U.S. PATENT DOCUMENTS

| | | | |
|---|---|---|---|
| 4,642,090 A | 2/1987 | Utrata | |
| 4,719,915 A | 1/1988 | Porat et al. | |
| 5,057,082 A * | 10/1991 | Burchette, Jr. | A61B 17/3417 606/167 |
| 5,071,426 A | 12/1991 | Dolgin et al. | |
| 5,423,824 A * | 6/1995 | Akerfeldt | A61B 17/3472 606/180 |
| 5,843,108 A | 12/1998 | Samuels | |
| 6,048,354 A | 4/2000 | Lawrence | |
| 6,110,175 A | 8/2000 | Scholl | |
| 6,224,574 B1 | 5/2001 | Al-Labban | |
| 6,270,501 B1 | 8/2001 | Freiberg et al. | |
| 6,346,115 B1 | 2/2002 | Lawrence | |
| 6,383,179 B1 | 5/2002 | Neuberger | |
| 6,497,687 B1 | 12/2002 | Blanco | |
| 6,761,726 B1 | 7/2004 | Findlay et al. | |
| 6,960,164 B2 | 11/2005 | O'Heeron | |
| 7,097,642 B1 | 8/2006 | Sprague et al. | |
| 7,144,414 B2 | 12/2006 | Harvie et al. | |
| 7,320,694 B2 | 1/2008 | O'Heeron | |
| 9,566,086 B2 | 2/2017 | Tebbe et al. | |
| 10,034,674 B2 | 7/2018 | Chudik | |
| 2004/0220497 A1 | 11/2004 | Findlay et al. | |

(Continued)

FOREIGN PATENT DOCUMENTS

DE        203 18 220 U1    3/2004

*Primary Examiner* — Nicholas W Woodall

(74) *Attorney, Agent, or Firm* — Carlson, Gaskey & Old, P.C.

(57) ABSTRACT

Surgical systems and methods for percutaneously inserting surgical devices, such as during glenoid labrum repairs or rotator cuff repairs of the shoulder, for example, may include a cannula and a cutting obturator insertable through the cannula. The cutting obturator may include a cutting tip configured for penetrating and dilating tissue during a percutaneous insertion into a joint space.

17 Claims, 7 Drawing Sheets

(56) References Cited

U.S. PATENT DOCUMENTS

| | | |
|---|---|---|
| 2006/0008771 A1* | 1/2006 | Courvoisier .......... A61B 17/16 |
| | | 433/165 |
| 2006/0015066 A1 | 1/2006 | Turieo et al. |
| 2008/0045965 A1 | 2/2008 | Miller et al. |
| 2008/0262318 A1 | 10/2008 | Gorek et al. |
| 2013/0331840 A1* | 12/2013 | Teisen ................ A61B 17/1615 |
| | | 606/80 |
| 2015/0142038 A1 | 5/2015 | Melsheimer |
| 2016/0051306 A1* | 2/2016 | Sasaki ................ A61B 17/8802 |
| | | 606/86 R |

\* cited by examiner

SURGICAL SYSTEMS FOR PERCUTANEOUSLY INSERTING SURGICAL DEVICES

BACKGROUND

This disclosure relates to surgical systems for percutaneously inserting surgical devices.

Suture anchors are used in many orthopedic surgical procedures to attach suture to bone. Once attached, the suture can be used to secure soft tissue to the bone. Suture anchors may be inserted through an arthroscopic cannula or percutaneously (i.e., through the skin).

SUMMARY

A surgical system for percutaneously inserting a surgical device according to an exemplary aspect of the present disclosure includes, among other things, a cannula and a cutting obturator insertable through the cannula and including a cutting tip. The cutting tip includes a hollow cylindrical body and two or more cutting blades that protrude radially outwardly from an outer surface of the hollow cylindrical body.

In a further non-limiting embodiment of the foregoing surgical system, the cannula is comprised of a transparent material and includes a hub having a first threaded portion that is adapted to engage a second threaded portion of a handle of the cutting obturator.

In a further non-limiting embodiment of either of the foregoing surgical systems, at least a portion of the cutting tip protrudes beyond a distal end portion of the cannula when the cutting obturator is received within the cannula.

In a further non-limiting embodiment of any of the foregoing surgical systems, the cutting obturator includes a tubular body, and the tubular body and the cutting tip together establish an inner lumen of the cutting obturator.

In a further non-limiting embodiment of any of the foregoing surgical systems, the cutting tip is integrally formed with a distal portion of the tubular body.

In a further non-limiting embodiment of any of the foregoing surgical systems, the cutting tip is a separate piece from the tubular body and includes an inner shaft that is received within the tubular body.

In a further non-limiting embodiment of any of the foregoing surgical systems, the tubular body includes a plastic material, and the cutting tip includes a metallic material.

In a further non-limiting embodiment of any of the foregoing surgical systems, the two or more cutting blades are equidistantly circumferentially spaced about the outer surface of the hollow cylindrical body.

In a further non-limiting embodiment of any of the foregoing surgical systems, each of the two or more cutting blades includes a knife edge located at a leading end of the cutting blade.

In a further non-limiting embodiment of any of the foregoing surgical systems, the knife edge is disposed proximal to a flat distal-most end of the hollow cylindrical body.

In a further non-limiting embodiment of any of the foregoing surgical systems, the knife edge is tapered and extends at a sloped angle relative to a proximal body portion of the cutting blade.

In a further non-limiting embodiment of any of the foregoing surgical systems, opposed outer sides of the two or more cutting blades extend longitudinally and are parallel to one another.

In a further non-limiting embodiment of any of the foregoing surgical systems, the surgical system is part of a surgical instrument set that further includes a guidewire.

In a further non-limiting embodiment of the forgoing surgical instrument set, the set includes a spinal needle.

A surgical method according to another exemplary aspect of the present disclosure includes, among other things, inserting a needle through a skin of a patient. The needle establishes a trajectory for percutaneously accessing a joint space underlying the skin. The method may further include inserting a guidewire through a cannulation of the needle, and inserting a surgical system over the guidewire. The surgical system includes a cannula and a cutting obturator received through the cannula. The method may further include rotating the surgical system into the skin until a cutting tip of the cutting obturator and a distal end portion of the cannula are positioned within the joint space, and then removing the cutting obturator from the cannula.

In a further non-limiting embodiment of the foregoing method, the method includes pressing the surgical system into the skin during the rotating.

In a further non-limiting embodiment of either of the foregoing methods, the method includes penetrating and dilating a tissue located between the skin and the joint space during the rotating.

In a further non-limiting embodiment of any of the foregoing methods, the method includes removing a trocar from the needle prior to inserting the guidewire through the cannulation of the needle and removing the needle after inserting the guidewire.

In a further non-limiting embodiment of any of the foregoing methods, the method includes inserting a surgical instrument into the joint space through the cannula after removing the cutting obturator.

In a further non-limiting embodiment of any of the foregoing methods, the cutting tip includes a hollow cylindrical body and two or more cutting blades that protrude radially outwardly from an outer surface of the hollow cylindrical body.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows

DETAILED DESCRIPTION

This disclosure relates to surgical systems and methods for percutaneously inserting surgical devices, such as during glenoid labrum repairs or rotator cuff repairs of the shoulder, for example. Exemplary surgical systems may include a cannula and a cutting obturator insertable through the cannula. The cutting obturator may include a cutting tip configured for penetrating and dilating tissue during percutaneous insertions into a joint space. These and other features of this disclosure are discussed in greater detail in the following paragraphs of this detailed description.

Figure 1:
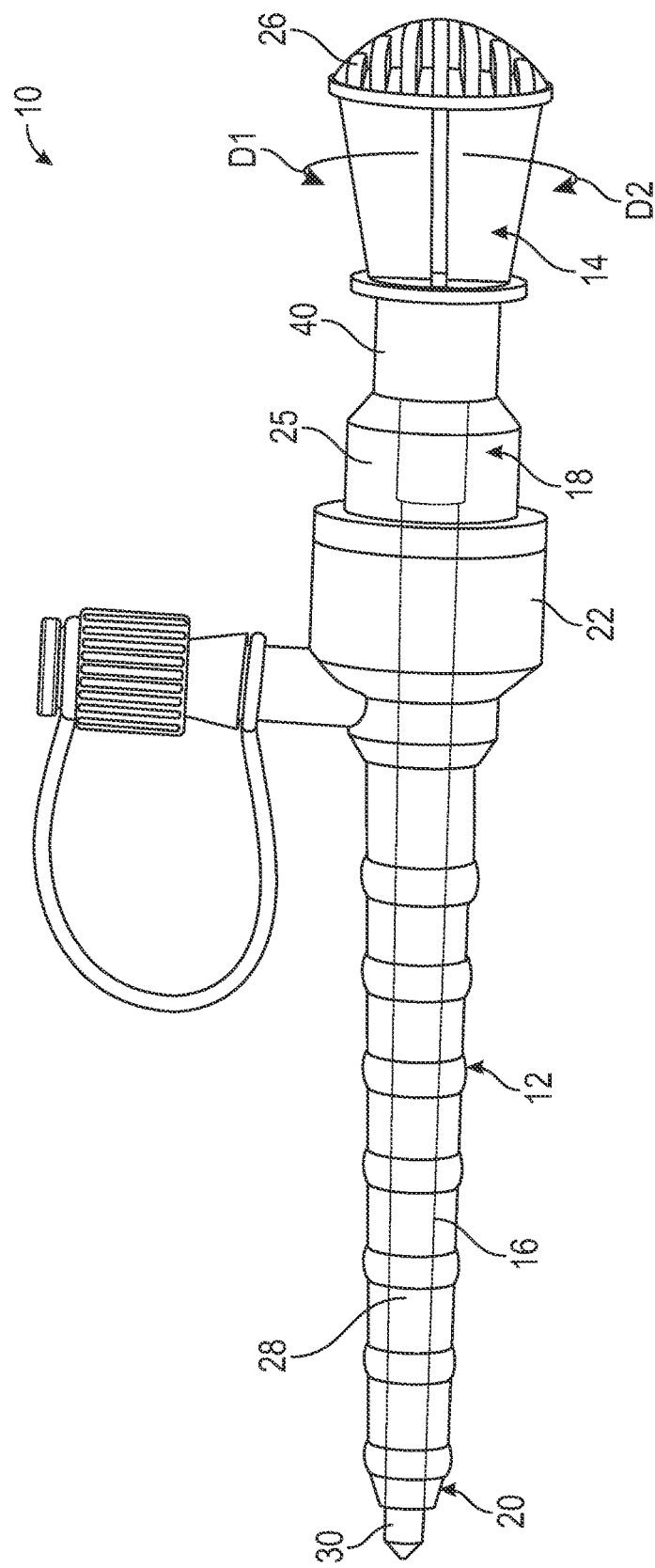
FIG. 1 illustrates a surgical system for performing a surgical procedure.
Figure 2:
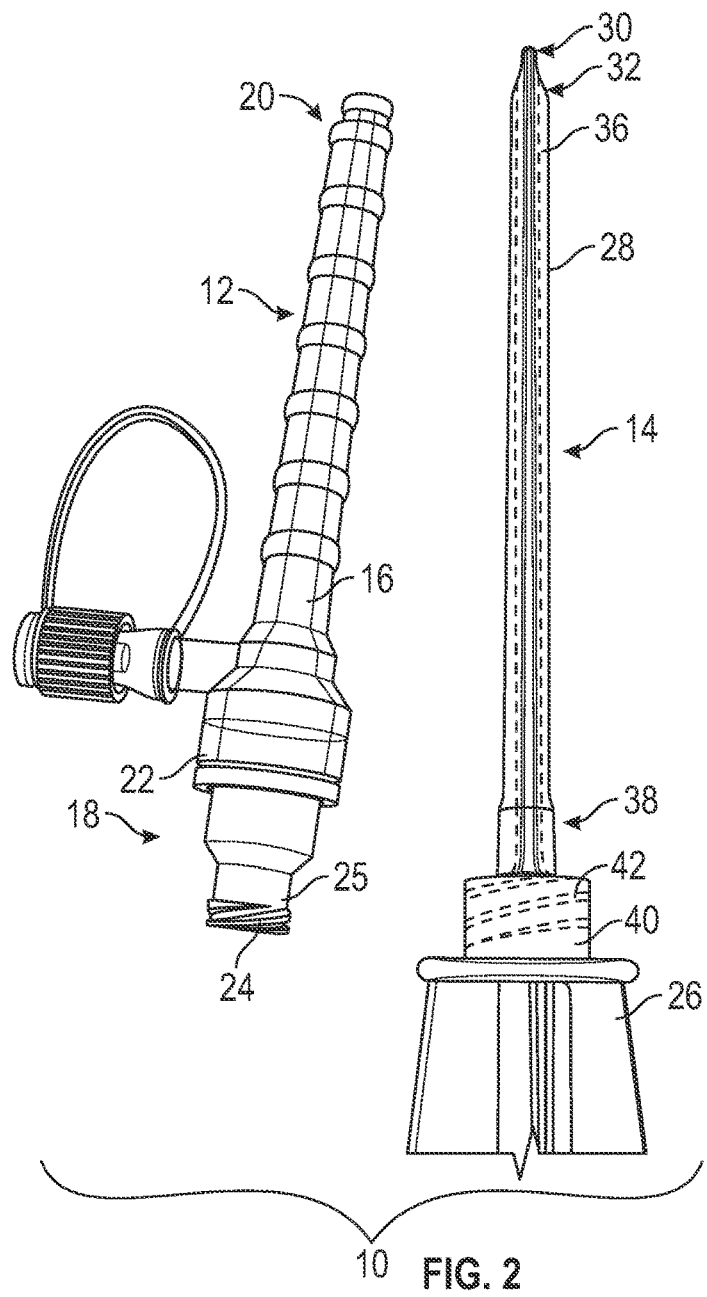
FIG. 2 is an exploded view of the surgical system of FIG. 1.

FIGS. 1-2 illustrate a surgical system 10 for performing orthopedic surgical procedures that involve the percutaneous insertion of surgical devices. In this disclosure, the term "percutaneous" refers to surgical procedures in which access to tissue or other underlying joint anatomies is achieved by puncturing or piercing through the patient's skin rather than by using either an open surgical approach or an arthroscopic surgical approach performed through an arthroscopic cannula or other portal. Exemplary orthopedic surgical procedures that can benefit from the percutaneous insertion of surgical devices include glenoid labrum repairs and rotator cuff repairs of the shoulder. However, the surgical system 10 of this disclosure could be utilized for performing various other orthopedic surgical procedures performed at various other locations of the human musculoskeletal system.

The surgical system 10 may include a cannula 12 and a cutting obturator 14 that is insertable through an internal bore 16 of the cannula 12. As further discussed below, the cannula 12 and the cutting obturator 14 may be used together as an assembly for percutaneously inserting and maneuvering the cannula 12 through soft tissue and into a targeted joint space during an orthopedic surgical procedure.

The cannula 12 extends longitudinally between a proximal end portion 18 and a distal end portion 20. The internal bore 16 extends longitudinally from the proximal end portion 18 to the distal end portion 20 and thus extends across an entire length of the cannula 12. The cutting obturator 14 may extend beyond the distal end portion 20 when received within the internal bore 16 of the cannula 12.

The proximal end portion 18 of the cannula 12 includes a hub 22 adapted for removably coupling the cutting obturator 14 to the cannula 12. A proximal-most section 25 of the hub 22 may include a threaded portion 24 adapted to connect to a handle 26 of the cutting obturator 14. However, other coupling arrangements between the cannula 12 and the cutting obturator 14 are also contemplated within the scope of this disclosure.

The cannula 12 of the surgical system 10 may be made from a transparent material. The transparent material may be a transparent polymeric material that permits the transmission of light through the cannula 12. The transparency of the cannula 12 permits the direct visualization of instruments inserted therethrough and of the anatomical structures surrounding the cannula 12, such as via an endoscope, during orthopedic surgical procedures.

The cutting obturator 14 may include a tubular body 28 and a cutting tip 30. When the cutting obturator 14 is received within the cannula 12, at least a portion of the cutting tip 30 protrudes beyond the distal end portion 20 of the cannula 12. Together, the tubular body 28 and the cutting tip 30 may establish an inner lumen 36 for using the cutting obturator 14 over a guidewire for providing targeted insertion of the surgical system 10 into a joint space.

In an embodiment, the cutting tip 30 is integrally formed with a distal portion 32 of the tubular body 28 (see FIG. 2).

Figure 3:
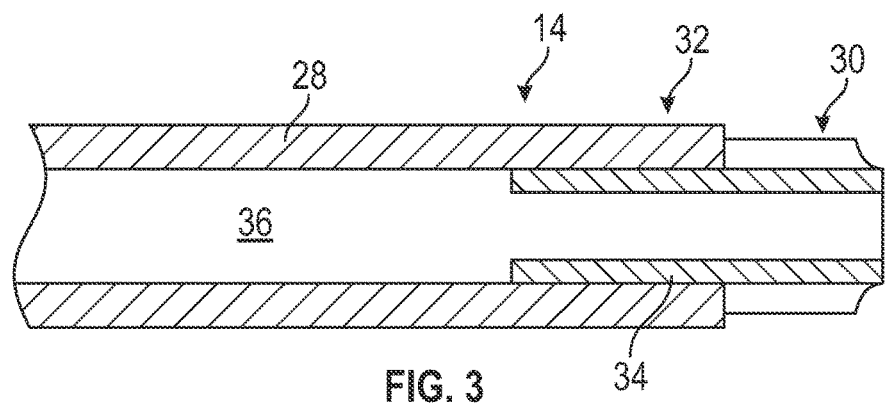
FIG. 3 illustrates select portions of an exemplary cutting obturator of the surgical system of FIGS. 1-2.

In another embodiment, the cutting tip 30 is a separate piece from the tubular body 28 and includes an inner shaft 34 that is received within the tubular body 28 (see FIG. 3). The distance the inner shaft 34 extends into the tubular body 28 is not intended to limit this disclosure.

The tubular body 28 and the cutting tip 30 may be made of various materials. For example, the tubular body 28 and the cutting tip 30 may be made of a metallic material, a polymeric blend, polyether ether ketone (PEEK), or any combination of these materials. In the embodiment of FIG. 3, the tubular body 28 may be made of a plastic material and the inner shaft 34 of the cutting tip 30 may be made of a metallic material. Other material configurations are also contemplated within the scope of this disclosure.

The handle 26 of the cutting obturator 14 may be secured at a proximal portion 38 of the tubular body 28. The handle 26 may include a distally-extending hub 40. A threaded portion 42 may be provided on an inner diameter surface of the hub 40. The threaded portion 42 is adapted to engage the threaded portion 24 of the cannula 12 for removably connecting the cutting obturator 14 to the cannula 12. The handle 26 of the cutting obturator 14 may be twisted or rotated in a first direction D1 (e.g., clockwise) to connect the cutting obturator 14 to the cannula 12, and may be twisted or rotated in a second, opposite direction D2 (e.g., counter-clockwise) to disengage the cutting obturator 14 from the cannula 12.

Figure 4:
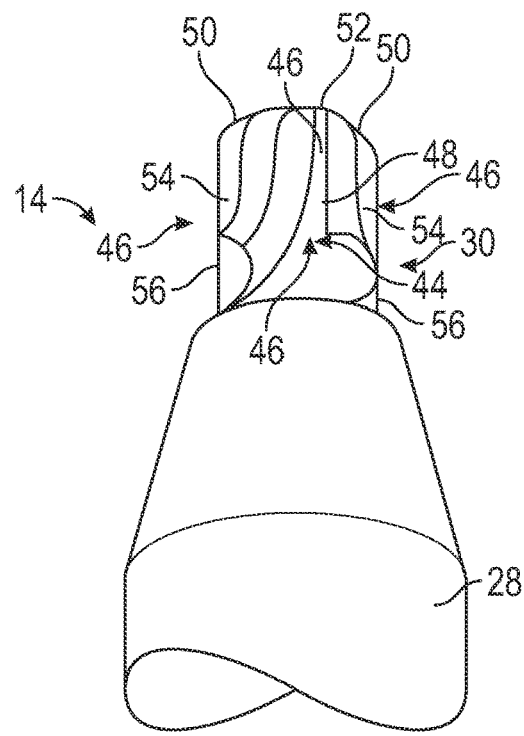
FIG. 4 illustrates a cutting tip of an exemplary cutting obturator of the surgical system of FIGS. 1-2.
Figure 5:
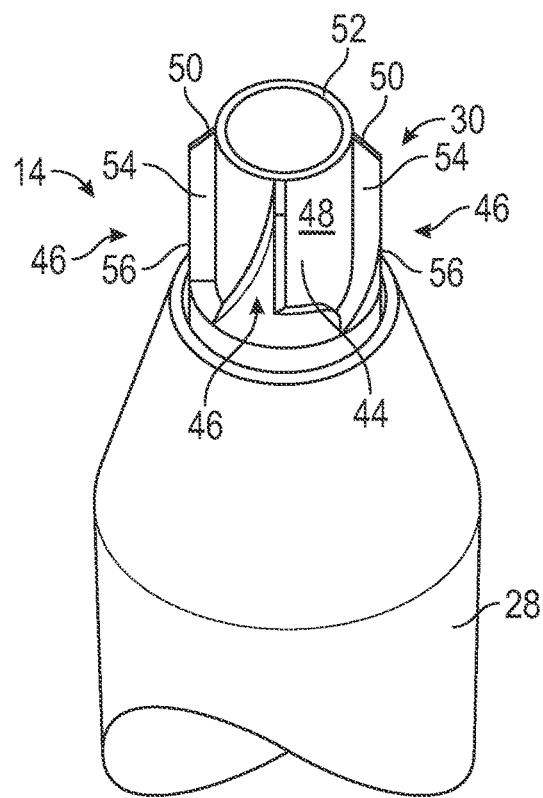
FIG. 5 is another view of the cutting tip of FIG. 4.

The cutting tip 30 of the cutting obturator 14 is further illustrated with reference to FIGS. 4-5. The cutting tip 30 may include a hollow cylindrical body 44 and two or more cutting blades 46 (e.g., 2, 3, 4, etc.) that protrude radially outwardly from an outer surface 48 of the hollow cylindrical body 44. In an embodiment, the cutting blades 46 are equidistantly circumferentially spaced about the outer surface 48.

Each cutting blade 46 may include a knife edge 50 located at a leading end of the cutting blade 46. In an embodiment, the knife edges 50 are located just proximal to a flat distal-most end 52 of the hollow cylindrical body 44. However, the knife edges 50 could alternatively extend to the flat distal-most end 52. The knife edges 50 may be tapered and may extend at a sloped angle relative to a proximal body portion 54 (e.g., a cutting flute) of the cutting blade 46. The taper/slope of each knife edge 50 provides for a dilating insertion technique of the surgical system 10 while requiring minimal to no skin incision. In an embodiment, opposed outer sides 56 of the cutting blades 46 extend longitudinally and are parallel to one another.

In an embodiment, the cutting blades 46 are formed by removing material from the cutting tip 30, altering the cutting tip 30 by adding an insert or material, or molding the cutting tip 30 to shape to form two or more cutting flutes that each include the knife edge 50 at their leading ends. The cutting tip 30 may be formed like a drill point to facilitate insertion through skin/tissue. The cutting flutes may project outwardly relative to the outer surface 48 of the hollow cylindrical body 44 to allow ease of insertion and removal of cut material while maintaining strength and stiffness at the cutting tip 30 of the cutting obturator 14.

FIGS. 6-15, with continued reference to FIGS. 1-5, schematically illustrate an exemplary surgical method involving the percutaneous insertion of surgical devices. The unique design of the surgical system 10 assists with penetrating and dilating tissue during its percutaneous insertion into a joint space. Fewer or additional steps than are recited below could be performed within the scope of this disclosure, and the recited order of steps depicted in FIGS. 6-15 is not intended to limit this disclosure.

Figure 6:
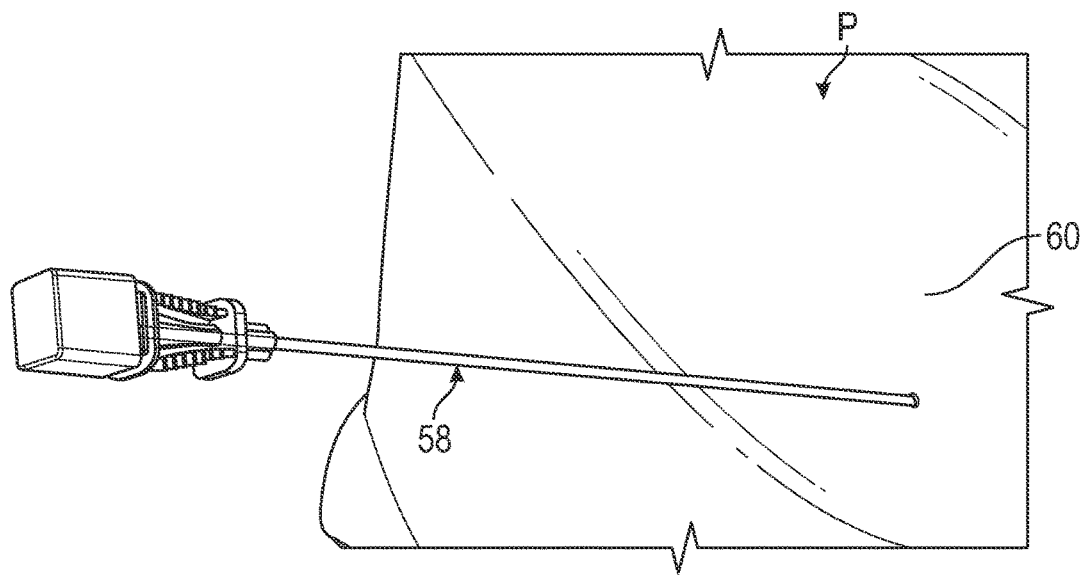
FIGS. 6, 7, 8, 9, 10, 11, 12, 13, 14, and 15 schematically illustrate an exemplary surgical method for percutaneously inserting surgical devices.
Figure 7:
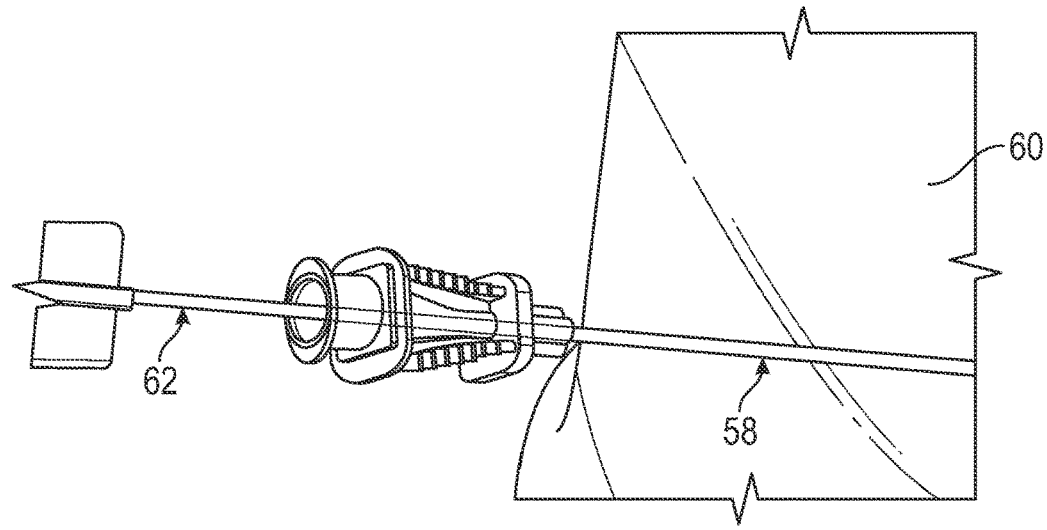

Referring first to FIG. 6, a spinal needle 58 may be inserted through a skin 60 of a patient P and into an underlying joint space. The spinal needle 58 may be used to locate and establish the correct trajectory and position for the subsequent percutaneous insertion of the surgical system 10 into the joint space. Once properly inserted, a trocar 62 may be removed from the spinal needle 58 (see FIG. 7).

Figure 8:
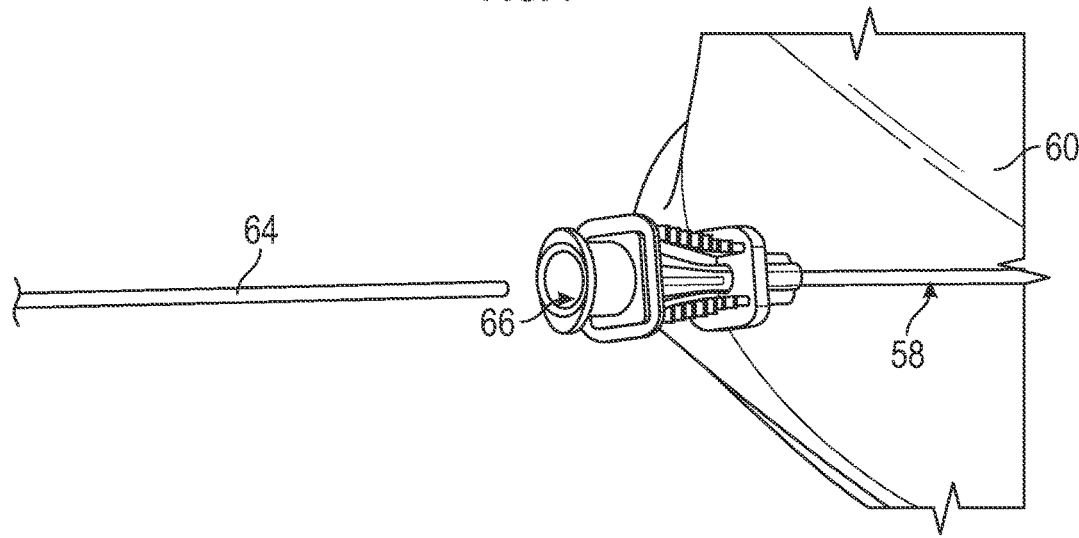
Figure 9:
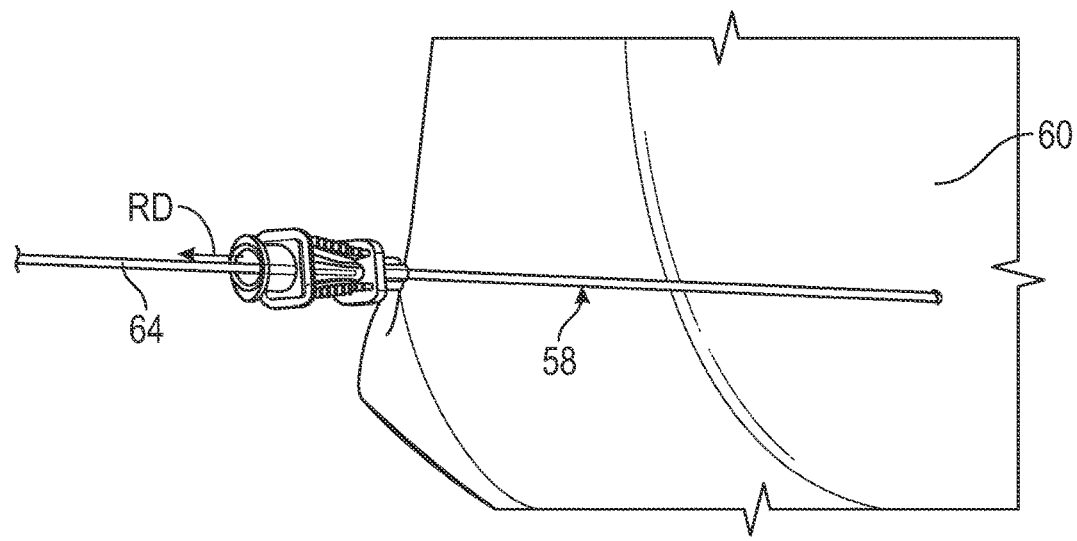
Figure 10:
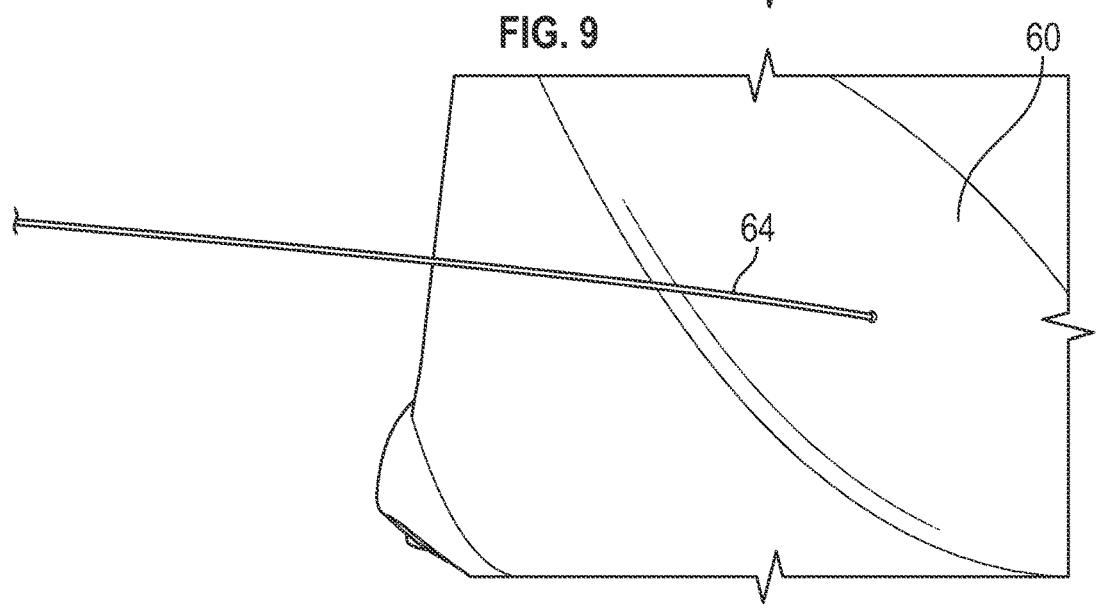

Next, as shown in FIG. 8, a guidewire 64, such as a nitinol guidewire, for example, may be inserted through a cannulation 66 of the spinal needle 58. The cannulation 66 is accessible upon removing the trocar 62 and extends entirely through the spinal needle 58. Upon full insertion of the guidewire 64, the spinal needle 58 may be removed by sliding the spinal needle 58 in a rearward direction RD over top of the guidewire 64 (see FIG. 9). FIG. 10 shows the guidewire 64 in a ready position for receiving the surgical system 10.

Figure 11:
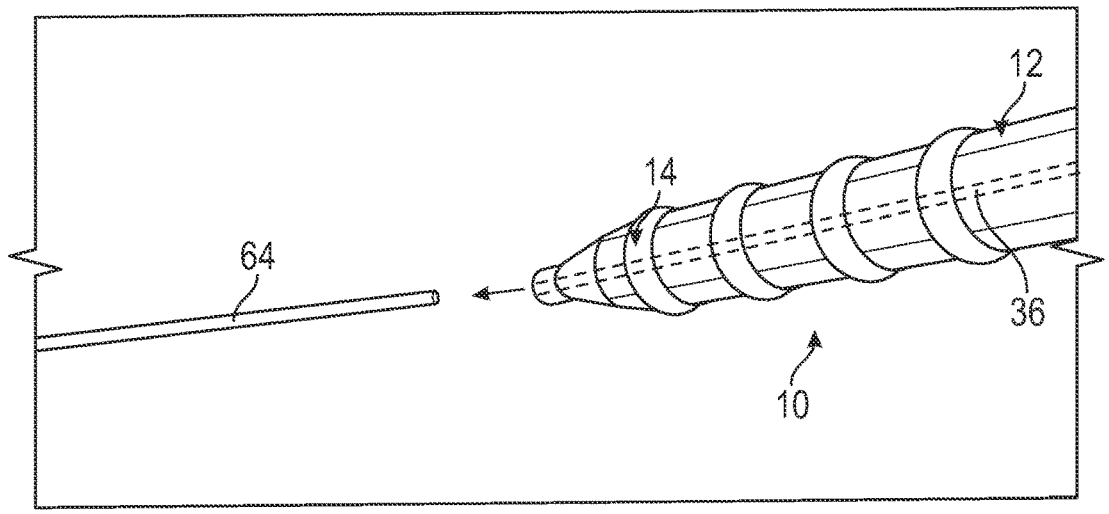
Figure 12:
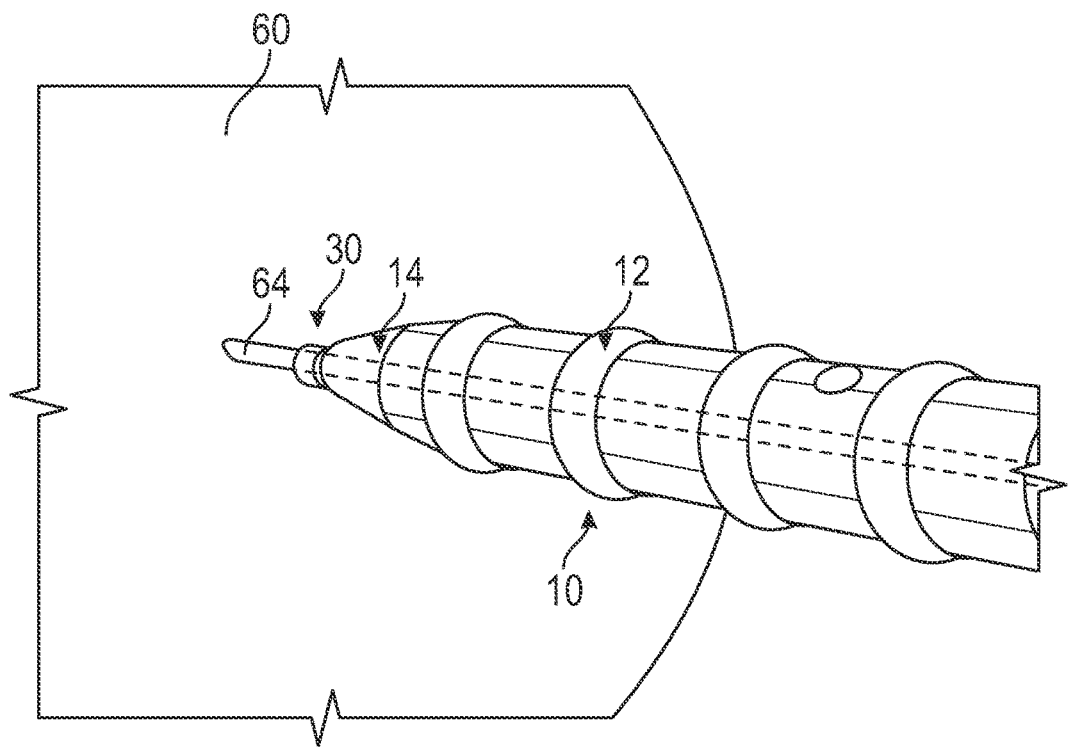

Referring to FIG. 11, the surgical system 10 may next be inserted over the guidewire 64. In an embodiment, the guidewire 64 is received within the inner lumen 36 of the cutting obturator 14 in order to position the surgical system 10 for the percutaneous insertion into a joint space underlying the skin 60. Once the guidewire 64 is received within the inner lumen 36, the surgical system 10 may be slid down over the guidewire 64 until the cutting tip 30 of the cutting obturator 14 contacts the skin 60 (see FIG. 12).

Figure 13:
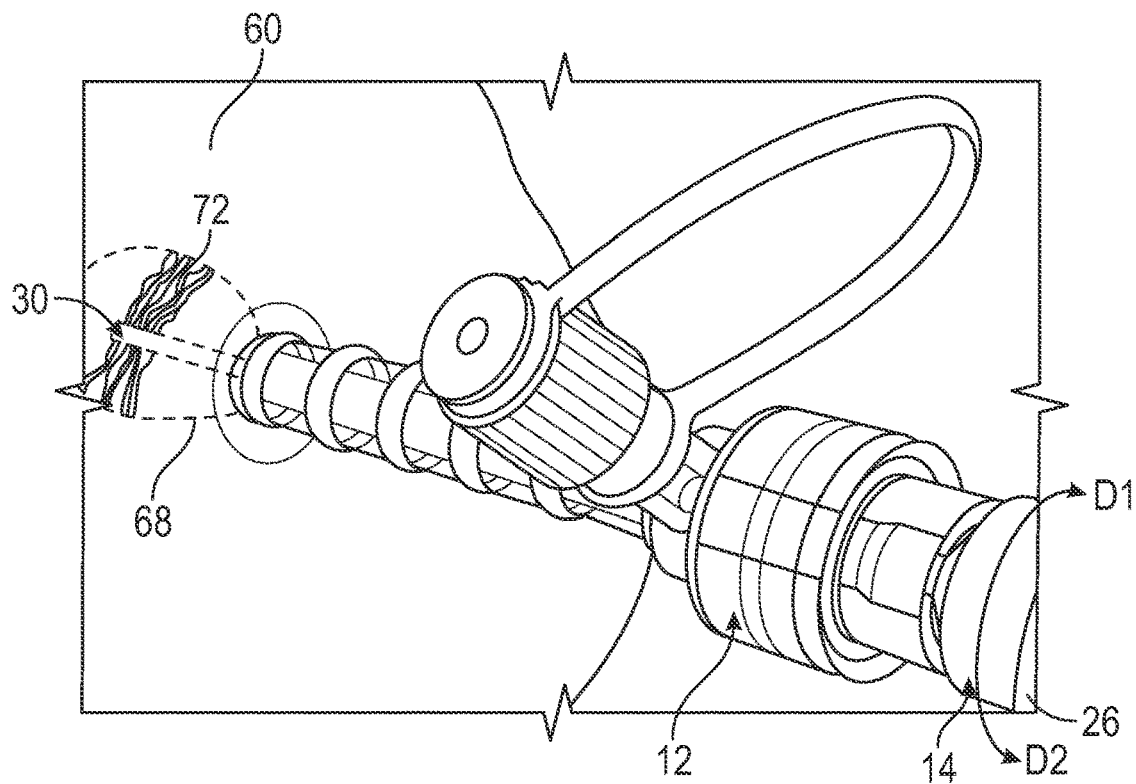
Figure 14:
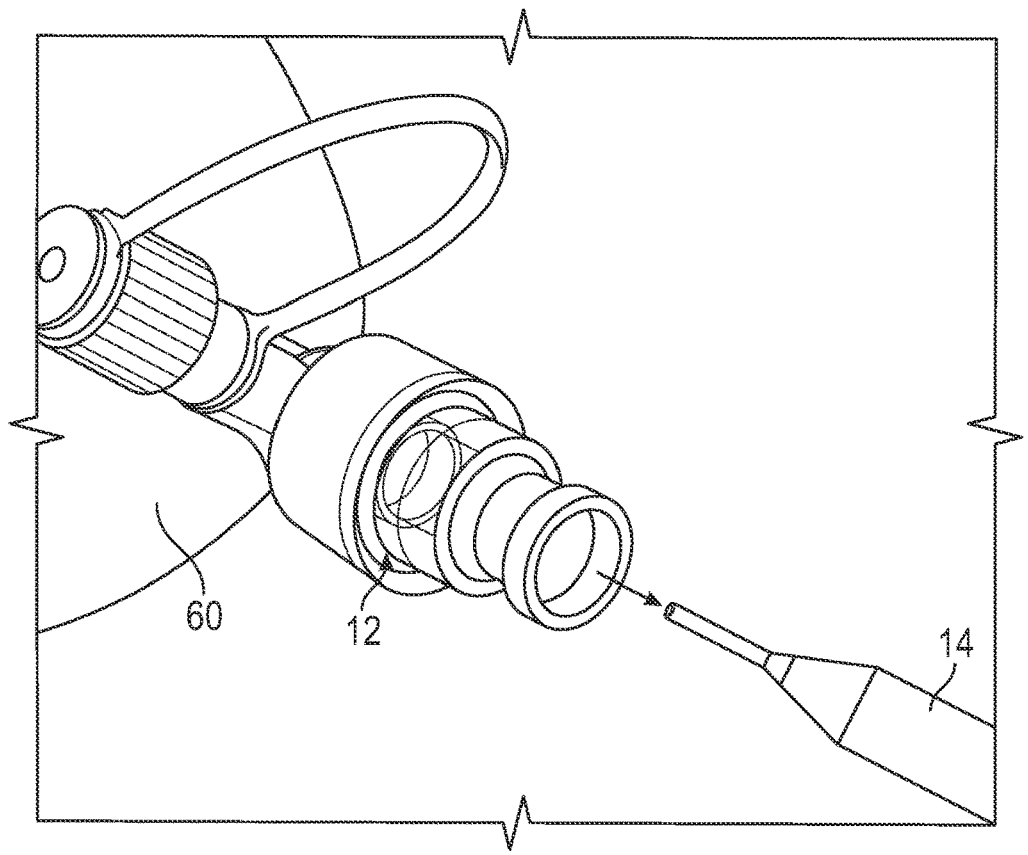

Next, as shown in FIG. 13, the cutting obturator 14 may be pressed and rotated in a direction D1 (e.g., a clockwise direction) into the skin 60 until the cutting tip 30 in inserted into the underlying joint space, which is schematically shown at reference numeral 68. The cutting blades 46 of the cutting tip 30 may penetrate and dilate tissue 72 located between the skin 60 and the underlying joint space 68 as the cutting obturator 14 is rotated further into the skin 60. Once a desired insertion distance is achieved, the handle 26 of the cutting obturator 14 may be rotated in a second, opposite direction D2 (e.g., counterclockwise) to disengage the cutting obturator 14 relative to the cannula 12. The cutting obturator 14 may then be removed from the cannula 12 (see FIG. 14).

Figure 15:
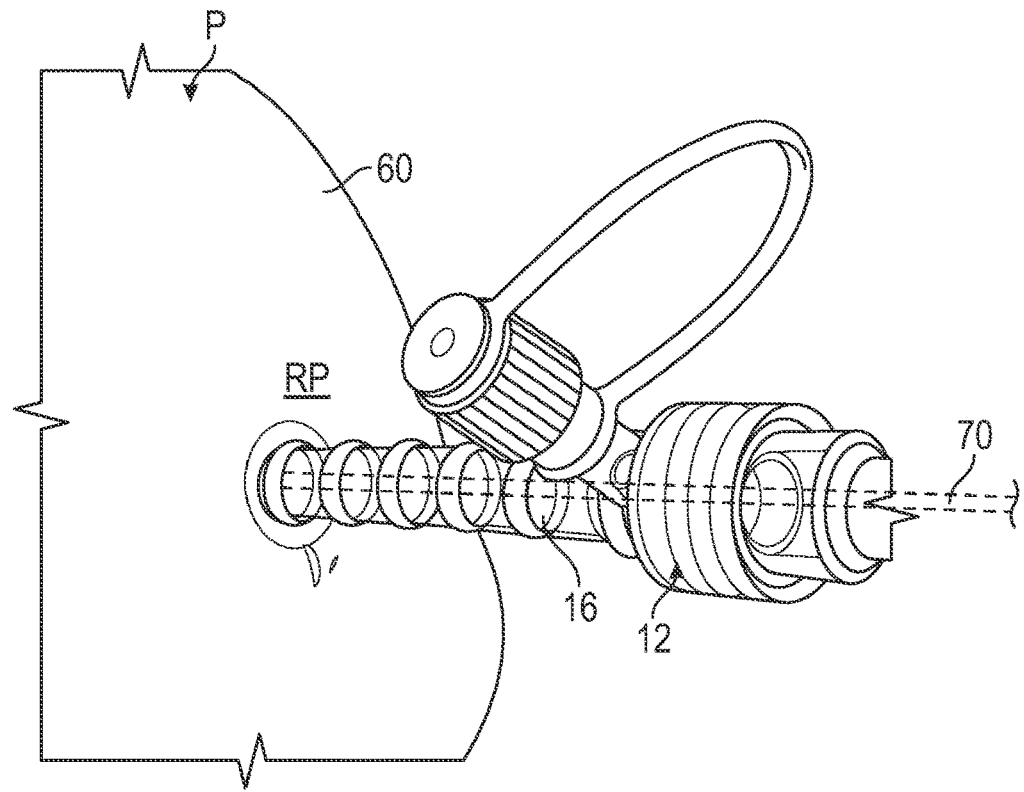

The cannula 12 is shown in a fully inserted and ready position RP in FIG. 15. In this position, the cannula 12 is ready to receive one or more surgical instruments 70, such as a drill guide, a drill, a suture anchor inserter, etc., for performing the desired orthopedic surgical procedure on the patient P. The surgical instruments 70 may be inserted through the internal bore 16 of the cannula 12.

The surgical system 10 described herein may be provided as part of a surgical instrument set. For example, the surgical system 10 could be packaged together as a kit with other surgical instruments, such as the spinal needle 58 and/or the guidewire 64, for formulating the surgical instrument set.

The surgical systems of this disclosure provide for the percutaneous insertion of surgical instruments. In some embodiments, a cannula of the surgical system may be precisely positioned and placed within an underlying joint space by using a dilating insertion technique that can be achieved via the use of a cutting obturator of the surgical system. The cannula may then facilitate the insertion of additional surgical instruments. Minimal to no skin incisions are required for achieving the percutaneous insertion of the cannula and the additional surgical instruments. The proposed surgical systems reduce surgical operating times and associated surgical costs.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical system for percutaneously inserting a surgical device, comprising:
    a cannula; and
    a cutting obturator insertable through the cannula and including a tubular body and a cutting tip,
    wherein the cutting tip includes a hollow cylindrical body and two or more cutting blades that protrude radially outwardly from an outer surface of the hollow cylindrical body,
    wherein the tubular body and the hollow cylindrical body of the cutting tip together establish an inner lumen of the cutting obturator,
    wherein the hollow cylindrical body of the cutting tip includes a flat distal-most end.

2. The surgical system as recited in claim 1, wherein the cannula is comprised of a transparent material and includes a hub having a first threaded portion that is adapted to engage a second threaded portion of a handle of the cutting obturator.

3. The surgical system as recited in claim 1, wherein at least a portion of the cutting tip protrudes beyond a distal end portion of the cannula when the cutting obturator is received within the cannula.

4. The surgical system as recited in claim 1, wherein the cutting tip is integrally formed with a distal portion of the tubular body.

5. The surgical system as recited in claim 1, wherein the cutting tip is a separate piece from the tubular body and includes an inner shaft that is received within the tubular body.

6. The surgical system as recited in claim 5, wherein the tubular body is comprised of a plastic material and the cutting tip is comprised of a metallic material.

7. The surgical system as recited in claim 1, wherein the two or more cutting blades are equidistantly circumferentially spaced about the outer surface of the hollow cylindrical body.

8. The surgical system as recited in claim 1, wherein each of the two or more cutting blades includes a knife edge located at a leading end of the cutting blade.

9. The surgical system as recited in claim 8, wherein the knife edge is disposed proximal to the flat distal-most end of the hollow cylindrical body.

10. The surgical system as recited in claim 8, wherein the knife edge is tapered and extends at a sloped angle relative to a proximal body portion of the cutting blade.

11. The surgical system as recited in claim 1, wherein opposed outer sides of the two or more cutting blades extend longitudinally and are parallel to one another.

12. The surgical system as recited in claim 1, wherein the inner lumen extends across an entire length of the tubular body.

13. A surgical instrument set, comprising:
the surgical system of claim 1; and
a guidewire.

14. The surgical instrument set as recited in claim 13, comprising a spinal needle.

15. The surgical instrument set as recited in claim 14, wherein the spinal needle is cannulated.

16. A surgical instrument set, comprising:
a surgical system for percutaneously inserting a surgical device, wherein the surgical system includes a cannula and a cutting obturator insertable through the cannula and including a tubular body and a cutting tip, wherein the cutting tip includes a hollow cylindrical body and two or more cutting blades that protrude radially outwardly from an outer surface of the hollow cylindrical body, wherein the tubular body and the hollow cylindrical body of the cutting tip together establish an inner lumen of the cutting obturator;
a guidewire;
a spinal needle, wherein the spinal needle is cannulated; and
a trocar removably received within the spinal needle.

17. A surgical system for percutaneously inserting a surgical device, comprising:
a cannula that includes an internal bore; and
a cutting obturator insertable through the internal bore and including a tubular body, a cutting tip including a hollow cylindrical body having two or more cutting blades that protrude radially outwardly from an outer surface of the hollow cylindrical body, and an inner lumen that extends through the tubular body and the hollow cylindrical body,
wherein the inner lumen is sized to accommodate a guidewire,
wherein the hollow cylindrical body of the cutting tip includes a flat distal-most end that is circular shaped.

* * * * *